United States Patent
Spanoudaki et al.

(10) Patent No.: US 9,645,252 B2
(45) Date of Patent: May 9, 2017

(54) METHOD TO EXTRACT PHOTON DEPTH-OF INTERACTION AND ARRIVAL TIME WITHIN A POSITRON EMISSION TOMOGRAPHY DETECTOR

(71) Applicant: The Board of Trustees of the Leland Stanford Junior University, Palo Alto, CA (US)

(72) Inventors: Virginia Ch Spanoudaki, Cambridge, MA (US); Craig Steven Levin, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 166 days.

(21) Appl. No.: 14/369,107

(22) PCT Filed: Dec. 27, 2012

(86) PCT No.: PCT/US2012/071862
§ 371 (c)(1),
(2) Date: Jun. 26, 2014

(87) PCT Pub. No.: WO2013/101956
PCT Pub. Date: Jul. 4, 2013

(65) Prior Publication Data
US 2014/0353510 A1      Dec. 4, 2014

Related U.S. Application Data

(60) Provisional application No. 61/580,957, filed on Dec. 28, 2011.

(51) Int. Cl.
*G01T 1/16*      (2006.01)
*G01T 1/20*      (2006.01)
(Continued)

(52) U.S. Cl.
CPC .......... *G01T 1/1644* (2013.01); *G01T 1/2002* (2013.01); *G01T 1/202* (2013.01);
(Continued)

(58) Field of Classification Search
CPC ... G01T 1/1644; G01T 1/2002; G01T 1/2004; G01T 1/2006; G01T 1/202
See application file for complete search history.

(56) References Cited

U.S. PATENT DOCUMENTS 7,601,963 B2    10/2009  Aykac
2005/0087692 A1* 4/2005  Romanov ............ G01T 1/2002
                                                    250/363.03
(Continued)

FOREIGN PATENT DOCUMENTS

WO    WO 2013/101956    7/2013

OTHER PUBLICATIONS

Shibuya et al. "Timing Resolution Improvement Using DOI Information in a Four-Layer Scintillation Detector for TOF-PET," Nucl. Inst. Meth. Phys. Res. A, 593 (2008), p. 572-577.*
(Continued)

*Primary Examiner* — Casey Bryant
(74) *Attorney, Agent, or Firm* — Beyer Law Group LLP

(57) ABSTRACT

A method for extracting photon depth-of-interaction of an incident photon in a crystal with a reflective coating optically coupled to all sides of the crystal, except for an opening, wherein a photodetector is optically coupled to the opening. A pulse shape of a photodetector output as a result of detection of scintillation photons from the crystal generated by the incident photon is measured, wherein the reflective coating optically coupled to all sides of the crystal, except for an opening optically coupled to the photodetector reflects the scintillation photons passing to all sides of the crystal, except for the opening optically coupled to the
(Continued)

photodetector. The pulse shape is used to determine photon depth-of-interaction within the crystal.

26 Claims, 6 Drawing Sheets

(51) Int. Cl.
A61B 6/00 (2006.01)
G01T 1/164 (2006.01)
G01T 1/202 (2006.01)
A61B 6/03 (2006.01)

(52) U.S. Cl.
CPC ............ *G01T 1/2006* (2013.01); *A61B 6/037* (2013.01); *A61B 6/4241* (2013.01); *A61B 6/508* (2013.01); *A61B 6/5205* (2013.01)

(56) References Cited

U.S. PATENT DOCUMENTS

2008/0284428 A1 11/2008 Fiedler et al.
2011/0108733 A1 5/2011 Omenge
2011/0174980 A1* 7/2011 Gagnon ................ G01T 1/2018
250/362

OTHER PUBLICATIONS

Ito et al., "Timing resolution improvement using DOI information in a four-layer scintillation detector for TOF-PET," Nuclear Instruments and Methods in Physics Research Section A: Accelerators, Spectrometers, Detectors and Associated Equipment vol. 593, Issue 3, Aug. 11, 2008, pp. 572-577.*
Seifert et al. "Monolithic LaBr3:Ce crystals on silicon photomultiplier arrays for time-of-flight positron emission tomography," Physics in Medicine and Biology Phys. Med. Biol. 57 (2012), pp. 2219-2233.*
Arafa et al., "Investigation of Different Wavelets for Pulse Shape Discrimination of LSO and LuYAP Scintillators in Positron Emission Tomography", Computer Engineering & Systems, 2009. ICCES 2009, DOI: 10.1109/ICCES.2009.5383058.*
International Search Report dated Apr. 29, 2014 from International Application No. PCT/US2012/071862.

* cited by examiner

METHOD TO EXTRACT PHOTON DEPTH-OF INTERACTION AND ARRIVAL TIME WITHIN A POSITRON EMISSION TOMOGRAPHY DETECTOR

CROSS REFERENCE TO RELATED APPLICATIONS

This application claims priority under 35 U.S.C. §119 from U.S. Provisional Patent Application No. 61/580,957, filed Dec. 28, 2011, entitled METHOD TO EXTRACT PHOTON DEPTH OF INTERACTION AND ARRIVAL TIME WITHIN A POSITRON EMISSION TOMOGRAPHY DETECTOR, which is incorporated herein by reference for all purposes.

FIELD OF THE INVENTION

A field of the invention is imaging. Example applications of the invention include, but are not limited to, nuclear imaging, nuclear medicine, clinical molecular imaging, or small animal molecular imaging.

BACKGROUND OF THE INVENTION

Positron emission tomography (PET) is a diagnostic imaging modality that is used to non-invasively measure the bio-distribution of a radioactive tracer. In positron emission tomography, a positron emitting bare radioactive isotope or an isotope that has been attached to a biomolecule is injected into a patient or animal. A positron is emitted by the radioactive isotope and annihilates with an electron producing two photons in opposite directions. Each of the photons has approximately 511 keV of energy, corresponding to the rest mass of the positron and electron. These two annihilation photons escape the patient and interact in a scanner that is positioned around the patient.

A scanner is made of arrays of high-energy photon detectors that convert interactions in the detector into electrical signals that are processed on subsequent electronics driven by a computer. An example of a high-energy photon detector is a scintillation crystal that is connected to an optical photodetector such as a photomultiplier tube or solid state photomultiplier. The photon is classified as high-energy because the photon has an energy of 511 keV, or kilo electron volt, which is much larger than optical photons that have energies in the 2-5 eV range. The annihilation photon can interact in the high atomic number, dense scintillation crystal, which in turn emits optical photons that bounce inside of the scintillation crystal. The optical photons propagate inside the crystal and are absorbed by a photodetector converting the light into an electrical signal. The electrical signal is then processed by analog and digital electronic circuits and is recorded as an event. The data acquisition electronics process the signal and record the time, location of the crystal or crystals that absorbed the high-energy photon and any secondary interaction processes, and the energy of the incoming high-energy photon to storage. In positron emission tomography, the two photons are paired by their timestamps to produce a line-of-response (LOR) of the interaction. These LORs are processed by image reconstruction algorithms to produce 3-D images of the distribution of the radiotracer.

A time-of-flight scanner is one where the arrival times of the photons are recorded to such an extent that the annihilation location can be estimated with a given resolution. Because photons travel at the speed of light, the annihilation location can be estimated by the following equation: $\Delta x = \Delta t / (2*c)$, where $\Delta x$ is the location of the annihilation measured from the center of the line, $\Delta t$ is the difference in time measured by the detectors, and $c$ is the speed of light.

SUMMARY OF THE INVENTION

Embodiments of the invention provide a method for extracting photon depth-of-interaction of a photon in a crystal with a reflective coating optically coupled to all sides of the crystal, except for an opening, wherein a photodetector is optically coupled to the opening. A pulse shape of a photodetector output as a result of detection of scintillation photons from the crystal generated by the incident photon is measured, wherein the reflective coating optically coupled to all sides of the crystal, except for an opening optically coupled to the photodetector reflects the scintillation photons passing to all sides of the crystal, except for the opening optically coupled to the photodetector. The pulse shape is used to determine photon depth-of-interaction within the crystal.

In another manifestation of the invention a method for extracting time-of-flight of a photon between its emission and its detection in a crystal with a reflective coating optically coupled to all sides of the crystal, except for an opening, wherein a photodetector is optically coupled to the opening is provided. A pulse shape of a photodetector output as a result of detection of scintillation photons from the crystal generated by the photon is measured, wherein the reflective coating optically coupled to all sides of the crystal, except for an opening optically coupled to the photodetector reflects the scintillation photons passing to all sides of the crystal, except for the opening optically coupled to the photodetector. The pulse shape is used to determine time-of-flight of a photon between its emission and its detection within the crystal.

In another manifestation of the invention a method for providing positron emission tomography, with plurality of crystals, wherein each crystal of the plurality of crystals with a reflective coating optically coupled to all sides of the crystal, except for an opening, wherein a photodetector is optically coupled to the opening is provided. A pulse shape of a photodetector output as a result of detection of scintillation photons from the crystal generated by an annihilation photon is provided, wherein the reflective coating optically coupled to all sides of the crystal, except for an opening optically coupled to the photodetector reflects the scintillation photons passing to all sides of the crystal, except for the opening optically coupled to the photodetector. The pulse shape is used to determine annihilation photon depth-of-interaction within the crystal. The pulse shape is used to determine annihilation photon time-of-flight between its emission and its detection within the crystal. The time-of-flight is used to determine a location of point of positron annihilation. The depth-of-interaction is used to refine the determined location of positron annihilation using time-of-flight along a line formed by two photodetector elements.

The invention and objects and features thereof will be more readily apparent from the following detailed description and appended claims when taken with the drawings.

DETAILED DESCRIPTION

Scanner

Figure 1A:
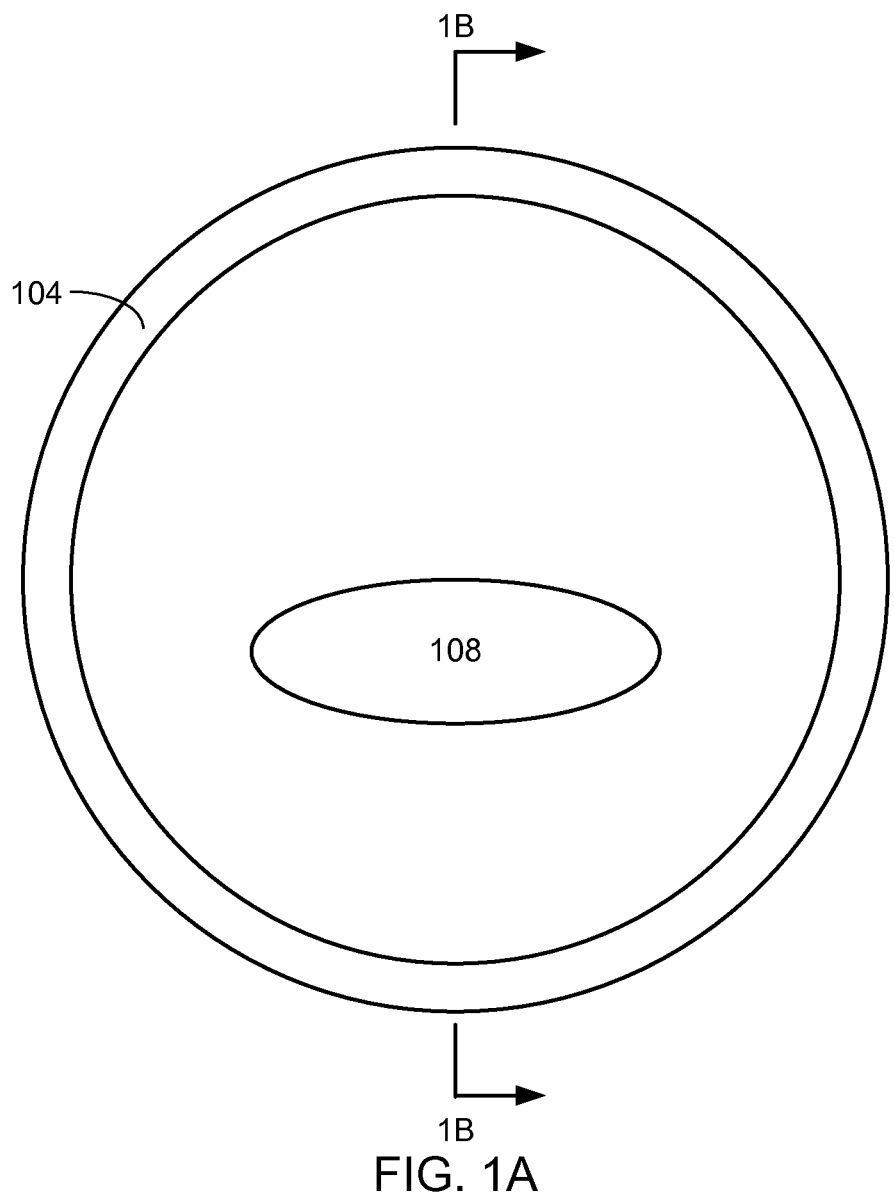
FIG. 1A is a cross sectional view of a depth-of-interaction scanner with an object, where the depth along the crystal is encoded using a special high-energy photon detector.
Figure 1B:
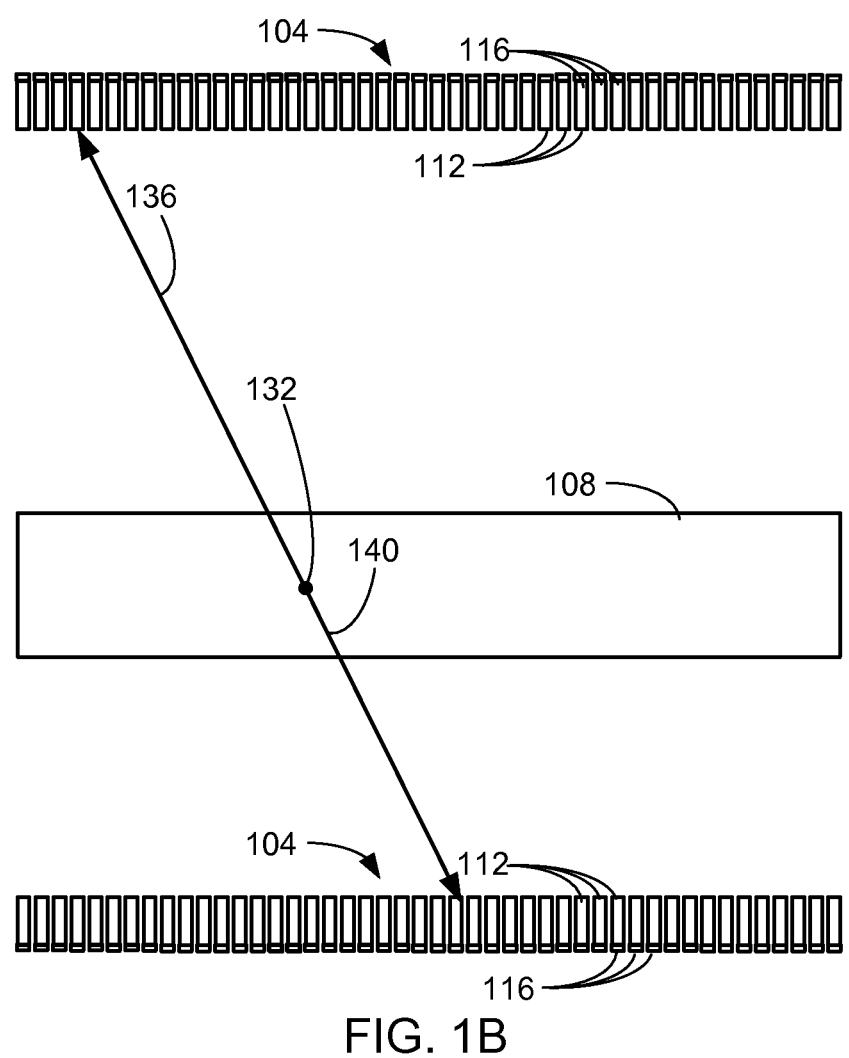
FIG. 1B is a cross sectional view of the depth-of-interaction scanner along cut line 1B that shows that the depth-of-interaction scanner is made of a plurality of individual scintillation crystals.

FIG. 1A is a cross sectional view of a depth-of-interaction PET scanner 104 with an object 108, where the depth along the crystal is encoded using a special high-energy photon detector. FIG. 1B is a cross sectional view of the depth-of-interaction PET scanner 104 along cut line 1B that shows that the depth-of-interaction PET scanner 104 is made of a plurality of individual scintillation crystals 112. Because the photon has significant depth of penetration in the scintillation crystal 112, significant blurring of the true line of response can occur. By recording the photon depth-of-interaction, this source of blurring is removed. Also, because the time-of-flight is important, the variance in the recorded depth in the detector also adds to the time-of-flight uncertainty. By incorporating depth-of-interaction with time-of-flight, this error can be minimized.

Figure 2:
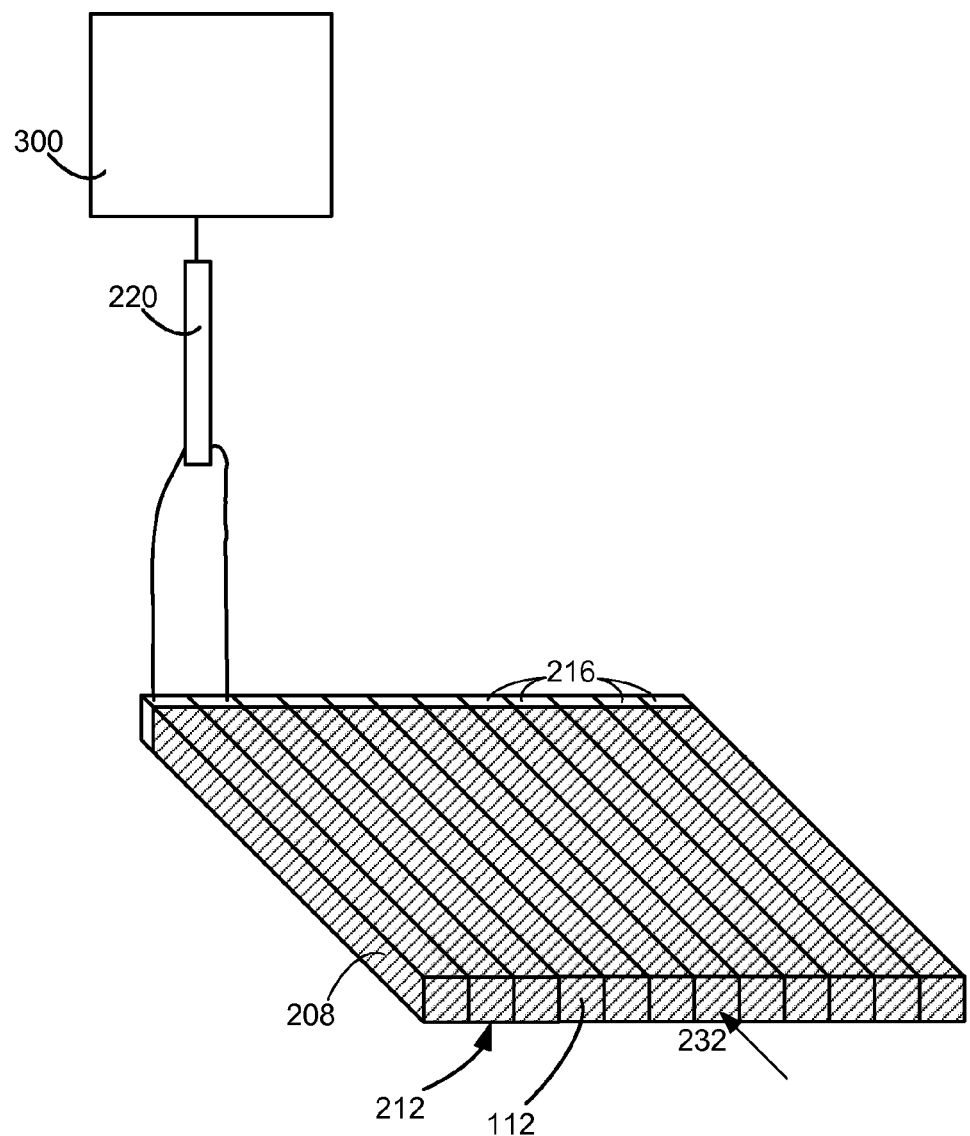
FIG. 2 is a perspective view of a row of scintillation crystals placed next to each other.

FIG. 2 is a perspective view of a row 212 of scintillation crystals 112 placed next to each other. Each scintillation crystal 112 is in the shape of a right rectangular prism. The longest dimension of each scintillation crystal 112 is the length, and the two shorter dimensions of each scintillation crystal 112 are widths. In this example, the two shorter dimensions are equal, so that an end of each scintillation crystal 112 is square. In other embodiments, the two shorter dimensions are not equal. Preferably, the length of the scintillation crystal 112 is greater than the widths of the scintillation crystal 112. More preferably, the length is at least five times longer than the widths. Preferably, the length of the scintillation crystal is sufficient to stop most of the incident high-energy photons. More preferably, the length of the scintillation crystal is at least 20 mm. A continuous reflective coating 208, shown as a shaded region, is formed over and optically coupled to five faces of each scintillation crystal 112. The scintillation crystals 112 are placed so that the lengths of each scintillation crystal 112 are parallel. Photodetectors 216 are placed adjacent to an end of the scintillation crystals 112, wherein the end of the scintillation crystals 112 is the face of the scintillation crystal that is not optically couple to or covered by the reflective coating 208. A circuit card 220 is electrically connected to at least one photodetector 216. The circuit card 220 is electrically connected to a computer system 300. Arrow 232 shows the path of the incident high-energy photon.

Figure 3:
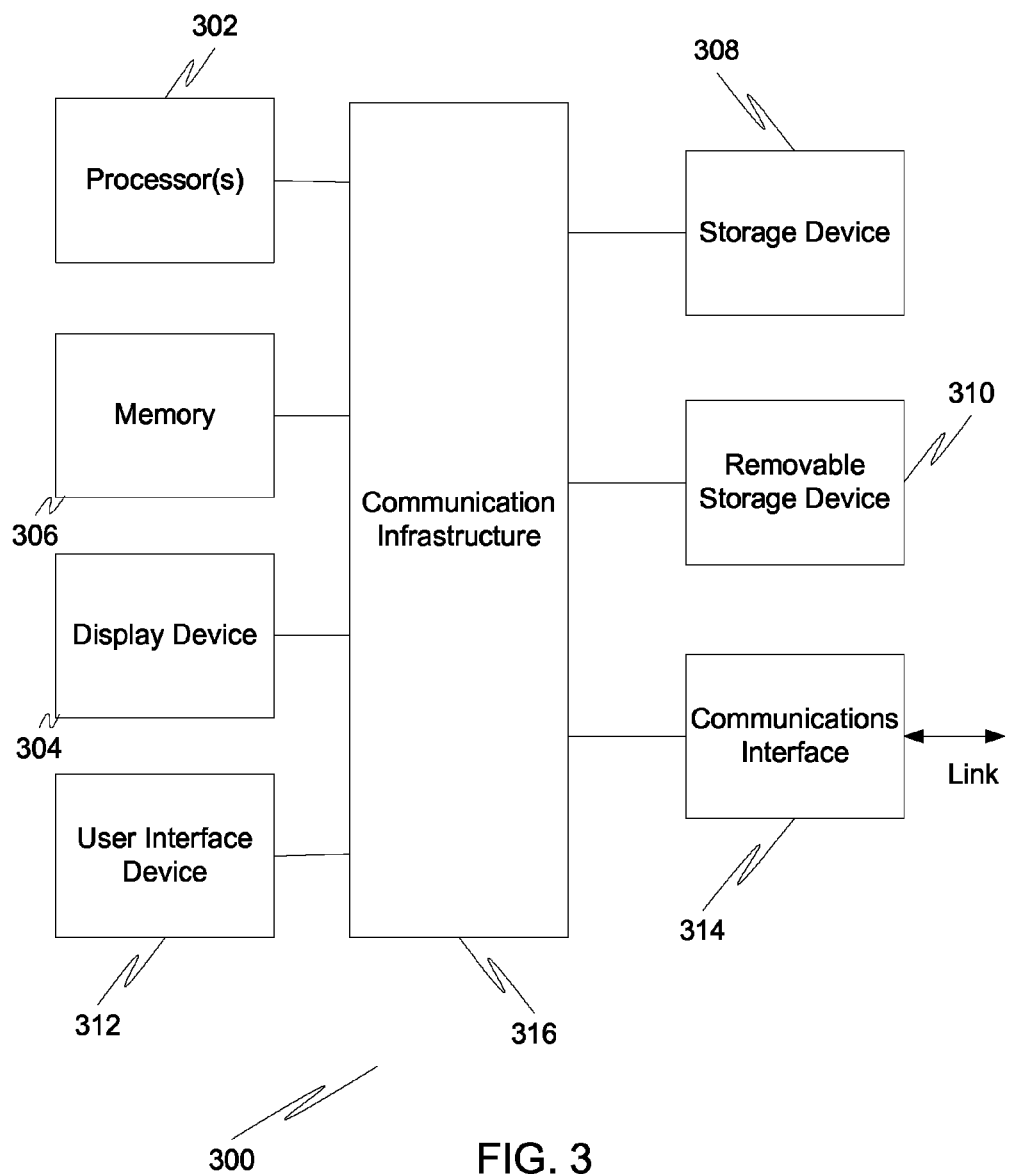
FIG. 3 is a high level block diagram showing a computer system used in an embodiment of the invention.

FIG. 3 is a high level block diagram showing a computer system 300, which may be used in an embodiment of the invention. The computer system may have many physical forms ranging from an integrated circuit, a printed circuit board, and a small handheld device up to a huge super computer. The computer system 300 includes one or more processors 302, and further can include an electronic display device 304 (for displaying graphics, text, and other data), a main memory 306 (e.g., random access memory (RAM)), storage device 308 (e.g., hard disk drive), removable storage device 310 (e.g., optical disk drive), user interface devices 312 (e.g., keyboards, touch screens, keypads, mice or other pointing devices, etc.), and a communication interface 314 (e.g., wireless network interface). The communication interface 314 allows software and data to be transferred between the computer system 300 and external devices via a link. The system may also include a communications infrastructure 316 (e.g., a communications bus, cross-over bar, or network) to which the aforementioned devices/modules are connected.

Information transferred via communications interface 314 may be in the form of signals such as electronic, electromagnetic, optical, or other signals capable of being received by communications interface 314, via a communication link that carries signals and may be implemented using wire or cable, fiber optics, a phone line, a cellular phone link, a radio frequency link, and/or other communication channels. With such a communications interface, it is contemplated that the one or more processors 302 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Operation

Figure 4:
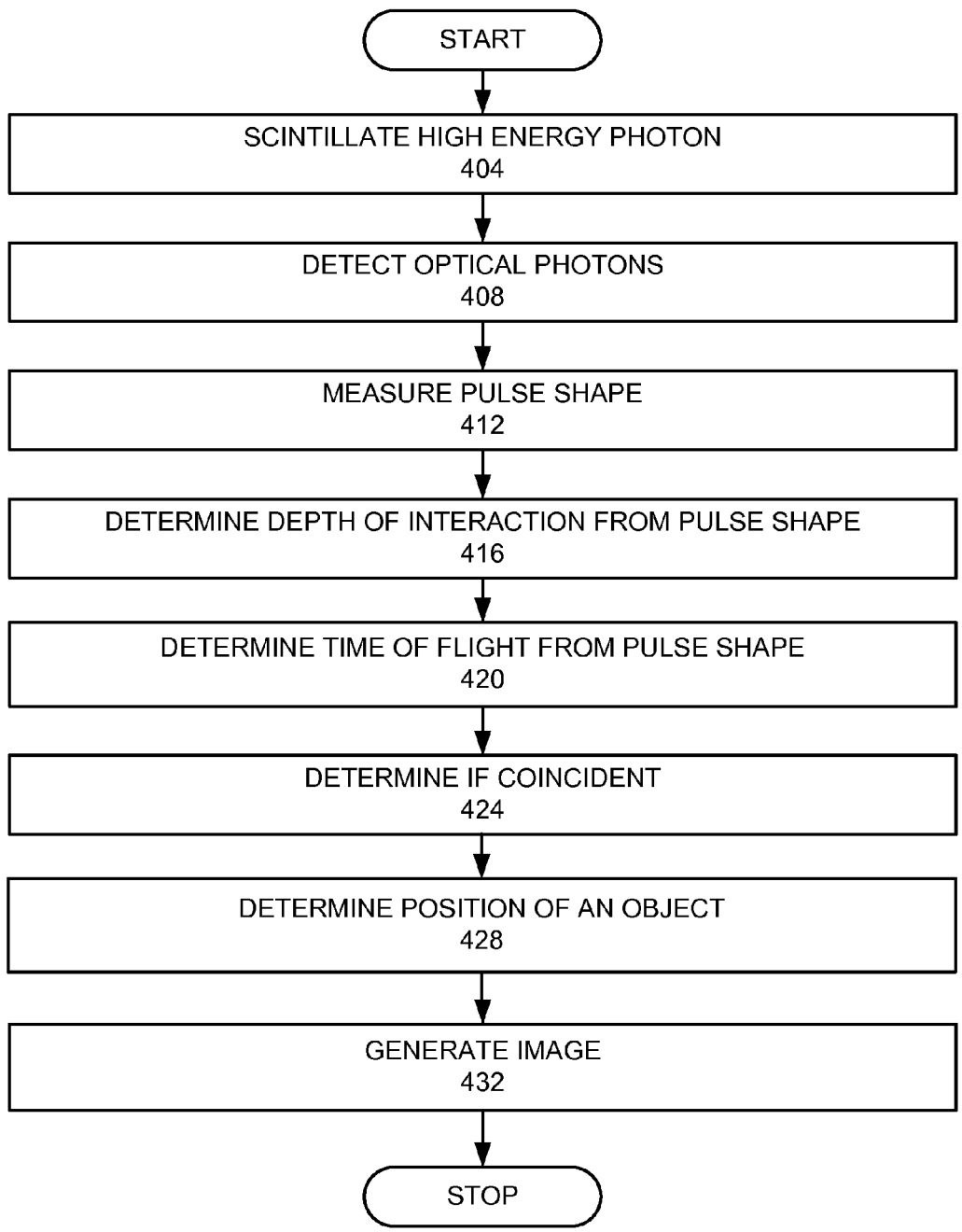
FIG. 4 is a high level flow chart of an embodiment of the invention.

FIG. 4 is a high level flow chart of an embodiment of the invention. A positron emitting isotope that has been attached to a chemical molecule is injected into a patient or animal. A positron is emitted by the radioactive isotope and annihilates with an electron producing two photons of high-energy in opposite directions. Each of the photons has approximately 511 keV of energy, corresponding to the rest mass of the positron and electron. FIG. 1B shows an annihilation location 132 of an annihilation event and a path 136 for a first high-energy annihilation photon and a path 140 for a second high-energy annihilation photon. These two high-energy annihilation photons escape the patient and interact with the PET scanner 104 that is positioned around the object 108. Each high-energy incident annihilation photon is absorbed in a scintillation crystal 112. The high-energy photons have an energy that allows them to pass through some objects like photodetectors 116, and therefore are often not detected by photodetectors 116. Because of this, the scintillation crystals 112 are used to absorb the high-energy photons after the high-energy photons have passed a significant distance into the scintillation crystals 112, and convert the high-energy photons into a larger number of lower energy optical scintillation photons, which may be detected by the photodetectors 116.

Figures 5A, 5B:
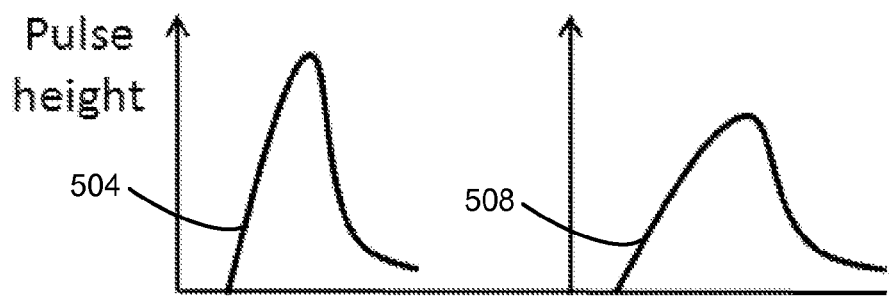
FIGS. 5A-B are illustrations of pulse shapes according to an embodiment of the invention.

A high-energy annihilation photon can interact in the high-Z (high atomic number) dense scintillation crystal, which in turn emits optical scintillation photons that bounce inside of the scintillation crystal. The optical photons propagate inside the crystal. If the optical photons reach five of the six surfaces, they are mostly reflected by the reflective coating. If the optical photons reach the only unreflective surface, they are mostly absorbed by a photodetector converting the light into an electrical signal. As a result, the optical photons are detected (step 408). The electrical signal is then processed by analog and digital electronic circuits and is recorded as an event. The data acquisition electronics process the signal and record the time and shape of the pulse (step 412). FIG. 5A and FIG. 5B are illustrations of a first pulse shape 504, and a second pulse shape 508.

Figures 6A, 6B:
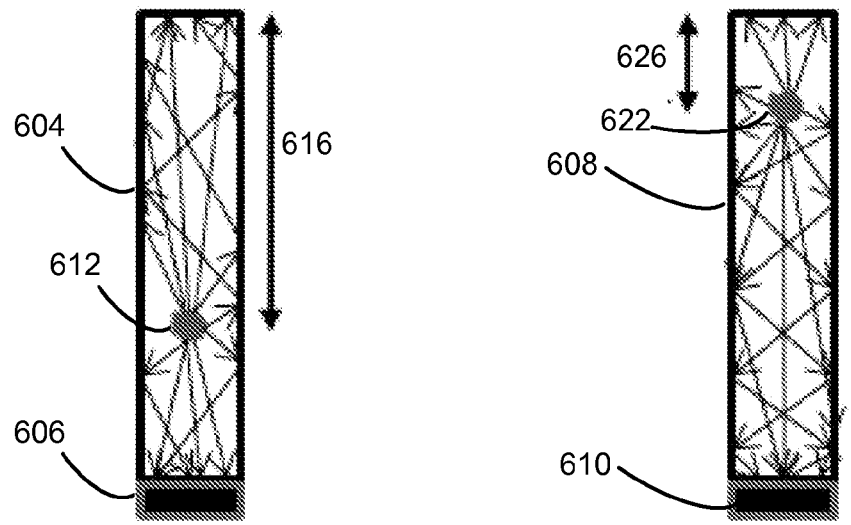
FIGS. 6A-B are schematic illustrations of scintillation crystals in an embodiment of the invention.

The depth-of-interaction is determined from the pulse shape (step 416). FIG. 6A and FIG. 6B are schematic illustrations of a first scintillation crystal 604 and a second scintillation crystal 608. The first scintillation crystal 604 has a first scintillation event 612 at a first depth-of-interaction (DoI) 616. The second scintillation crystal 608 has a second scintillation event 622 at a second DoI 626. The arrows within the first scintillation crystal 604 illustrate how the optical photons are reflected off of all sides of the first scintillation crystal 604 by the reflective coating, except for the side optically coupled to a first photodetector 606. Likewise, the arrows within the second scintillation crystal 608 illustrate how the optical photons are reflected off of all sides of the second scintillation crystal 608 by the reflective coating, except for the side optically coupled to a second photodetector 610. The difference in pulse shape may be attributed by the amount of scattering or reflection, the distance of the interaction from the photodetector and the distance of the interaction from the reflective surfaces. The pulse shape is dependent upon all of the surfaces reflecting and/or scattering the photons, except for the surfaces optically coupled to the photodetectors 606, 610. The pulse shape is also used to determine time-of-flight (step 420).

The timing of the signal is used to determine if there is a coincident signal (step 424). This may be accomplished by determining whether events happen within a certain time difference from each other. If two events are within a certain time difference from each other, the related photons are paired. If events are paired, the location of an object is determined (step 428). In positron emission tomography, the two photons are paired by their timestamps to produce a line-of-response (LOR) of the interaction. After the locations of annihilation events are determined, an image may be generated (step 432). These LORs are processed by image reconstruction algorithms to produce 3-D images of the distribution of the radiotracer. Better depth resolving capability of the depth-of-interaction detector will result in a more uniform spatial resolution. Preferably, time-of-flight information is used to determine the location of the annihilation, and then DoI is used to improve the resolution of the location.

Figure 7:
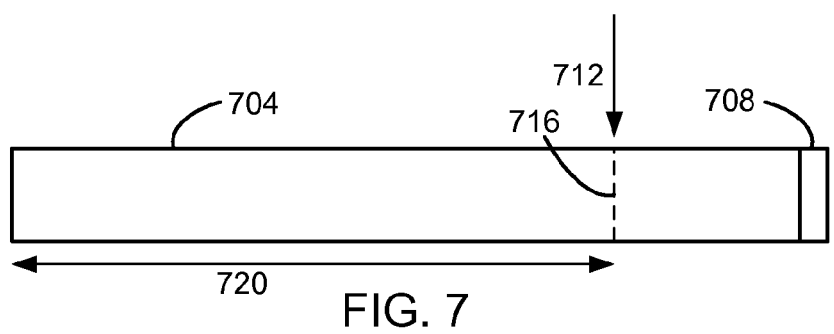
FIG. 7 illustrates how depth-of-interaction is calibrated in an embodiment of the invention.

Various methods may be used to determine DoI from pulse shape. In one embodiment, different pulse shapes are measured and calibrated to known DoI's in a lookup table. For example, a scintillation crystal may be exposed to an incident high-energy annihilation photons that pass through sideways, along a width, instead of along a length. FIG. 7 is a schematic view of a scintillation crystal 704 with an optically coupled photodetector 708. An incident high-energy annihilation photon is directed along a path as shown by the arrow 712, so that any scintillation event must be along dashed line 716, to provide the DoI 720. The known DoI can be matched with the measured pulse shape and a lookup table may be created. One or more of the following pulse shape characteristics may be used in a lookup table to determine DoI: pulse height, rise time, rise shape, decay time, decay shape, variance, time difference, and pulse width. In one embodiment, pulse height alone is used to determine DoI.

Time-of-flight may also be determined by pulse shape. In an embodiment, a position of an annihilation event is determined by time-of-flight. The resolution of the position may then be improved by determining DoI.

The different frequency components of the detector signal can be exploited in various ways in order to extract from them information such as photon detection time and DoI. For the extraction of time information, one ideally needs to probe the very early stages of a signal's rise which are mostly associated with the first scintillation photons reaching the photodetector window. At the same time, there is a need to suppress high frequency components associated with randomized electronic and photon noise. Thus, proper noise suppression (or signal denoising) that will enhance desired frequencies and suppress undesired ones may lead to more accurate time estimation. For the extraction of depth-of-interaction information, one ideally needs to identify frequency patterns (or time delays between characteristic frequency patterns) during the time evolution of the detector signal that are associated with DoI. In long and narrow crystal elements, the scattering of light may create delays in its detection compared to the amount of unscattered light that gets detected. These delays manifest themselves as subtle changes in the signal's frequency patterns that can be observed by proper isolation and enhancement of the transient signal shape details.

In order to achieve the above goals, some embodiments use multiresolution analysis (otherwise known as wavelets analysis). This analysis identifies the contributing frequencies in an electrical signal and, in addition, determines their time of occurrence with an optimal compromise between time and frequency resolution. The time dependent frequency identification (or frequency pattern identification) has a significant advantage of the wavelets over the Fourier analysis, since it allows not only identification of the frequencies in question, but in addition, it allows identification of which part of the signal (rise/fall) these frequencies are contributing to. A preferred embodiment primarily used the discrete wavelets transform (DWT) for pattern decomposition, which essentially decomposes the detector signal by subjecting it to a number of high- and low-pass filters, thus providing information about the approximations and the details of the signal. Depending on the decomposition level to which the signal is subject, the approximations are indicative of the denoised signal (for low decomposition levels) and can be used for accurate time estimation at the early stages of the pulse. The details are indicative of the intermediate frequency signal patterns (for high decomposition levels) that may correlate with the detection of a photon event or its DoI After extracting the photon detection time and DoI from the aforementioned multiresolution analysis, the detection time information and its variance are parameterized based on DoI. The parameterization formulas are extracted by experimentally determining how the mean and the full width at half maximum (FWHM) of a coincidence time histogram change as a function of DoI. In order to do that, the detector in this embodiment (a $3 \times 3 \times 20$ mm$^3$ Lutetium Oxyorthosilicate (LSO) crystal element read out from one side by a SiPM photodetector element) was irradiated sideways with an incident high-energy annihilation photon source (Ge-68) at different depths along the crystal element's thickness, as described above regarding FIG. 7. Electronic collimation is achieved by registering coincident annihilation photon events between the detector of interest and a small detector pixel placed on the opposite side of the source. The two detector signals are fully digitized and histograms of their detection time difference are registered for a predefined number of events forming a coincidence time histogram. The same measurement is repeated for different depth positions at which the source irradiates the length of the detector element of interest. The FWHM and mean of the resulting coincidence time histograms are subsequently plotted as a function of the source position which is the high-energy annihilation photon DoI. Curve fitting on those plots will yield the desired parameterization formulas:

$$t_1 = f(DoI_1)$$

$$t_2 = f(DoI_2)$$

$$\sigma t_1 = f(DoI_1)$$

$$\sigma t_2 = f(DoI_2)$$

where t and DoI are determined from the digitized signals with DWT, and f has been shown to best be represented by a second degree polynomial.

Using such a wavelet transform method to determine DoI with LSO crystals is expected to provide a DoI resolution of 10 mm. Using such a wavelet transform method to determine time-of-flight with LSO crystals is expected to provide a time resolution of 100-200 picoseconds.

Preferably, the length of the scintillation crystal is greater than the widths of the scintillation crystals. More preferably, the lengths of the scintillation crystals are at least five times greater than either of the widths of the scintillation crystal. Most preferably, the length of the scintillation crystal is at least ten times greater than either of the widths of the scintillation crystal. Preferably, each photodetector is connected to only one scintillation crystal.

In other embodiments of the inventions, crystals with different surface roughnesses and reflective surfaces are tested. For example, scintillation crystals with polished surfaces and a specular reflector may be measured as shown in FIG. 7. Pulse shape and DoI may be compared to determine if pulse shape may be used to determine DoI. Similar testing may be done on scintillation crystals with polished surfaces with a diffuse reflector, rough (granulated) crystal surfaces with a specular reflector, and rough (granulated) crystal surfaces with a diffuse reflector. The pulse shapes and DoI may be compared to determine if pulse shape may be used to determine DoI for any of these configurations. It is believed that an unpolished surface may increase the amount of light that is directed to the photodetector.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for extracting photon depth-of-interaction of an incident photon in a scintillation crystal with a reflective coating covering all sides of the crystal, except for an opening, wherein a photodetector is optically coupled to the opening, comprising:
   measuring a pulse shape of a photodetector output as a result of detection of scintillation photons from the crystal generated by the incident photon, wherein the reflective coating covers all sides of the crystal, except for an opening optically coupled to the photodetector reflects the scintillation photons passing to all sides of the crystal, wherein the scintillation photons passing to sides of the crystal are reflected off of all sides of the crystal covered by the reflective coating; and
   using the pulse shape to determine incident photon depth-of-interaction within the crystal.

2. The method, as recited in claim 1, further comprising using the pulse shape to determine time-of-flight of the incident photon.

3. The method, as recited in claim 2, further comprising using both the depth-of-interaction and time-of-flight of the incident photon to determine a position of an annihilation event along a PET system response line.

4. The method, as recited in claim 3, wherein the incident photon is an annihilation photon resulting from positron emission, wherein the determination of the position of the annihilation event along a PET system response line comprises identifying a coincident event.

5. The method, as recited in claim 4, wherein the using the pulse shape to determine time-of-flight of the incident photon, comprises using frequency pattern identification.

6. The method, as recited in claim 5, wherein the using the pulse shape to determine the incident photon depth-of-interaction within the crystal, comprises using pulse height to determine the incident photon depth-of-interaction within the crystal.

7. The method, as recited in claim 6, wherein the using frequency pattern identification used to determine time-of-flight of the incident photon comprises using frequency pattern decomposition.

8. The method, as recited in claim 5, wherein the using the pulse shape to determine the incident photon depth-of-interaction within the crystal, comprises using frequency pattern identification to determine the incident photon depth-of-interaction within the crystal.

9. The method, as recited in claim 8, wherein the crystal is a rectangular prism with a first width, a second width, and a length, wherein the length is at least five time greater than both the first width and the second width.

10. The method, as recited in claim 2, wherein the using the pulse shape to determine time-of-flight of the incident photon, comprises using frequency pattern identification.

11. The method, as recited in claim 2, wherein the using frequency pattern identification used to determine time-of-flight of the incident photon comprises using frequency pattern decomposition.

12. The method, as recited in claim 1, wherein the using the pulse shape to determine the incident photon depth-of-interaction within the crystal, comprises using pulse height to determine the incident photon depth-of-interaction within the crystal.

13. The method, as recited in claim 1, wherein the using the pulse shape to determine the incident photon depth-of-interaction within the crystal, comprises using frequency pattern identification to determine the incident photon depth-of-interaction within the crystal.

14. A method for extracting time-of-flight of an incident photon between its emission and its detection in a crystal with a reflective coating covering all sides of the crystal, except for an opening, wherein a photodetector is optically coupled to the opening, comprising:

measuring a pulse shape of a photodetector output as a result of detection of scintillation photons from the crystal generated by the incident photon, wherein the reflective coating covering all sides of the crystal, except for an opening optically coupled to the photodetector reflects the scintillation photons-passing to all sides of the crystal covered by the reflective coating; and using the pulse shape to determine time-of-flight of the incident photon between its emission and its detection in the crystal.

15. The method, as recited in claim 14, wherein the incident photon is an annihilation photon resulting from positron emission, wherein the determination of the position of the annihilation event comprises identifying a coincident event.

16. The method, as recited in claim 15, wherein the using the pulse shape to determine time-of-flight of the incident photon, comprises using frequency pattern identification.

17. A method for providing positron emission tomography, with plurality of crystals, wherein each crystal of the plurality of crystals with a reflective coating covering all sides of the crystal, except for an opening, wherein a photodetector is optically coupled to the opening, comprising:

measuring a pulse shape of a photodetector output as a result of detection of scintillation photons from the crystal generated by an annihilation photon, wherein the reflective coating covering all sides of the crystal, except for an opening optically coupled to the photodetector reflects the scintillation photons;

using the pulse shape to determine annihilation photon depth-of-interaction within the crystal;

using the pulse shape to determine annihilation photon time-of-flight between its emission and its detection within the crystal; and using the depth-of-interaction to refine the determined annihilation photon time-of-flight; and using the refined determined annihilation photon time-of-flight to determine a location of point of positron annihilation.

18. The method, as recited in claim 17, wherein the incident photon is an annihilation photon resulting from positron emission, wherein the determination of the position of the annihilation event comprises identifying a coincident event.

19. The method, as recited in claim 18, wherein the using the pulse shape to determine time-of-flight of the incident photon, comprises using frequency pattern identification.

20. The method, as recited in claim 19, wherein the using the pulse shape to determine the incident photon depth-of-interaction within the crystal, comprises using pulse height to determine the incident photon depth-of-interaction within the crystal.

21. The method, as recited in claim 20, wherein the using frequency pattern identification used to determine time-of-flight of the incident photon comprises using frequency pattern decomposition.

22. The method, as recited in claim 19, wherein the using the pulse shape to determine the incident photon depth-of-interaction within the crystal, comprises using frequency pattern identification to determine the incident photon depth-of-interaction within the crystal.

23. The method, as recited in claim 22, wherein the crystal is a rectangular prism with a first width, a second width, and a length, wherein the length is at least five time greater than both the first width and the second width.

24. A method for generating a photon depth-of-interaction lookup table for a crystal with a reflective coating optically coupled to all sides of the crystal, except for an opening, wherein a photodetector is optically coupled to the opening and wherein the crystal has a length, comprising:

directing incident photons into the scintillation crystal at different lengths of the scintillation crystal;

recording a pulse shape of a photodetector output as a result of the detection of the incident photon and a position of the incident photon along the length; and using the pulse shape and position of the incident photon along the length to generate a depth-of-interaction versus pulse shape lookup table.

25. The method, as recited in claim 24, wherein a variance and time difference of the pulse shape is used to generate the depth-of-interaction versus pulse shape lookup table.

26. The method, as recited in claim 1, wherein the pulse shape is a measure of pulse height versus time for a single scintillation event.

\* \* \* \* \*